United States Patent [19]

Becker et al.

[11] 4,026,948
[45] May 31, 1977

[54] PROCESS FOR THE PREPARATION OF 2,2,6-TRIMETHYL-CYCLOHEX-5-EN-1,4-DIONE

[75] Inventors: Joseph J. Becker, Geneva; Karl-Heinrich Schulte-Elte, Onex; Hugo Strickler, Dardagny; Günther Ohloff, Bernex, all of Switzerland

[73] Assignee: Firmenich S.A., Geneva, Switzerland

[22] Filed: Aug. 24, 1976

[21] Appl. No.: 717,209

Related U.S. Application Data

[63] Continuation of Ser. No. 527,450, Nov. 26, 1974, abandoned.

[30] Foreign Application Priority Data

Dec. 7, 1973  Switzerland .................. 17172

[52] U.S. Cl. .................................. 260/586 P
[51] Int. Cl.² .................. C07C 45/00; C07C 45/04
[58] Field of Search ........................ 260/586 P

[56] References Cited

UNITED STATES PATENTS

| | | | |
|---|---|---|---|
| 2,819,298 | 1/1958 | Isler et al. | 260/586 P |
| 2,917,539 | 12/1959 | Isler et al. | 260/586 P |
| 3,070,629 | 12/1962 | Ohloff et al. | 260/586 P |
| 3,404,185 | 10/1968 | Thomas et al. | 260/586 P |

OTHER PUBLICATIONS

*Chem. Process Review*, 66 "Cat. Manuf., Recovery and Use".
*J. Org. Chem.*, 36, 1446 (1971).
*J. Org. Chem.*, 37, 4067 (1972).
"The Oxidation of Hydrocarbons in the Liquid Phase", *Pergamon Press*, Oxford (1975).

*Primary Examiner*—Norman Morgenstern
*Attorney, Agent, or Firm*—Pennie & Edmonds

[57] ABSTRACT

Process for the preparation of a diketone derivative useful as perfuming and taste-modifying agent as well as intermediate for the preparation of compounds having utility in the pharmaceutical and dye-stuff industry.

3 Claims, No Drawings

1

PROCESS FOR THE PREPARATION OF 2,2,6-TRIMETHYL-CYCLOHEX-5-EN-1,4-DIONE

This is a continuation of application Ser. No. 527,450, filed Nov. 26, 1974, now abandoned.

SUMMARY OF THE INVENTION

This invention relates to the preparation of an alicyclic diketone having the formula

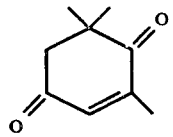

which compound is defined as being the 2,2,6-trimethyl-cyclohex-5-en-1,4-dione (hereinafter referred to as oxophorone).

More specifically, this invention relates to a process for the preparation of said diketone, which process comprises oxidizing, in the liquid phase, 3,3,5-trimethyl-cyclohex-4-en-1-one by means of oxygen, or an oxygen containing gas mixture, in the presence of a metal catalyst selected from the group consisting of a salt, an oxide and an organic derivative of a transition metal or copper.

BACKGROUND OF THE INVENTION 2,2,6-Trimethyl-cyclohex-5-en-1,4-dione and homologues thereof, are useful as starting materials in the synthesis of certain carotenoids (see e.g. O. Isler "Carotenoids" Birkhäuser Verlag, Basel, 1971, page 130) and are also useful in the fields of flavouring and perfumery (see e.g. U.S. Pat. No. 3,380,456). Several methods are known for the synthesis of such compounds, usually starting from isophorone, i.e. 3,3,5-trimethyl-cyclohex-5-en-1-one, which is commercially available at a low price and in practically unlimited quantities. One such method, described in Tetrahedron Suppl., 8, 1–7 (1966), Helv. Chim. Acta, 39, 2041 (1956) and U.S. Pat. No. 2,917,539, is summarized in the following reaction scheme:

However, this synthetic route suffers from the disadvantages of producing low yields of the desired diketone, of comprising several successive reaction steps, and of requiring the use of relatively expensive reagents, so that it is unsuitable for use on an industrial scale.

In order to provide an industrially more advantageous synthetic route, we have attempted to prepare 2,2,6-trimethyl-cyclohex-5-en-1,4-dione by oxidizing 4-bromo-3,5,5-trimethyl-cyclohex-2-en-1-one with nitropropane or with a tertiary amine oxide such as trimethylamine oxide. However, instead of the desired diketone, this reaction yeilded, 2,4,4-trimethyl-cyclohex-5-en-6-ol-1-one, i.e. the compound of formula

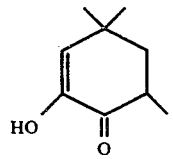

(see German Offenlegungsschrift No. 2,202,066).

The known method for the direct oxidation of an allylic methylene group to give the corresponding carbonyl derivative, by means of actinic irradiation in an aqueous medium in the presence of N-bromosuccinimide (see e.g. Chem. Comm., 1969, 1220), proved unsuccessful when applied to isophorone. Other known oxidation methods were also unsuccessful, including those described in J. Am. Chem. Soc. 79, 6308 (1957), J. Am. Chem. Soc. 83, 2952, (1961), J. Org. Chem. 33, 3566, (1968), Tetrahedron Letters 1972, 1823, and Liebigs Ann. Chem. 627,237, (1959): all of these methods either did not produce any appreciable amount of the desired ketone, or gave yields too poor for practical utility.

THE INVENTION

It has now surprisingly been found that good yields of oxophorone can be obtained by direct oxidation of 3,3,5-trimethyl-cyclohex-4-en-1-one, also known as β-phorone, by means of oxygen, or an oxygen containing gas mixture, in the presence of a metal catalyst selected from the group consisting of a salt, an oxide and an organic derivative of a transition metal or copper.

The transition metal of the oxidizing catalyst is preferably selected from the group consisting of vanadium, chromium, manganese, iron, cobalt and nickel. The oxidation can be effected in a homogeneous or heterogeneous system. In the first of the said oxidation modes, the chosen catalyst is preferably used on an inert solid support presenting a large surface, e.g. $SiO_2$, carbon, magnesium, or calcium carbonate or hydrogeno-carbonate, or a diatomaceous earth.

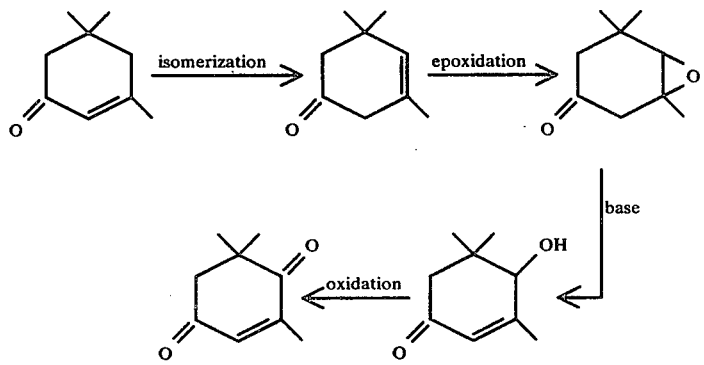

However, the best results are obtained by using the aforementioned oxidation catalysts in a homogeneous system, preferably under the form of an acetylacetonate or an acetate salt. These salts are commercially available at low price (e.g. from Fluka A.G., Buchs, Switzerland or Wacker GmbH, Munich, West Germany).

PREFERRED EMBODIMENTS OF THE INVENTION

In accordance with a preferred embodiment of the present invention, the oxidation is performed by means of manganese$^{II}$ acetate, manganese$^{III}$ acetate, cobalt$^{II}$ acetate, cobalt$^{II}$ acetylacetonate, chromium$^{III}$ acetylacetonate, vanadium$^{III}$ acetylacetonate, nickel$^{II}$ acetylacetonate or copper$^{II}$ acetylacetonate.

According to another preferred embodiment of this invention, the oxidation is effected by treating the starting material with the chosen oxidation reagent in a reaction vessel equipped with a particularly efficient stirring system. Such a system is very important, but not critical, for obtaining high yields of oxophorone by promoting a regular and homogeneous distribution of the oxidizing gas within the reaction mixture.

The oxidizing gas can be constituted by pure oxygen or mixtures containing oxygen together with an inert gas, e.g. nitrogen or argon. For all practical purposes, air, or oxygen enriched air mixtures, are preferred.

Pure oxygen and air can also be used in alternation, pure oxygen being preferably used at the beginning of the reaction for better initiating the oxidation process.

The proportions of pure oxygen present in the oxidizing gas mixture can vary within a wide range. For all practical purposes however a ratio of 4 parts of inert gas for 1 part of oxygen is used (air e.g.).

The flow of gas as well as its inlet pressure can also vary within a wide range, their choice is not critical and they can be selected by keeping into account the volume of starting material to be oxidized and the chosen reaction temperature.

According to another embodiment of this invention, the oxidation process is carried out in a reaction vessel equipped either with a gas compressor, or with a self-initiating gas mixer.

It is to be understood, however, that all devices which can enable a high fragmentation and a uniform distribution of the gas stream within the liquid reacting mixture, e.g. a sintered glass funnel, can be used.

A wide range of reaction temperatures can be used for the oxidation, but it is found that they are preferentially comprised between about 25° and 75° C. More preferably, the oxidation is performed at about 50° C.

β-Phorone, used as starting material in the process of the invention, can be prepared by isomerization of isophorone by means of a basic isomerization agent, said agent being a member selected from the group consisting of a hydroxide, e.g. KOH or NaOH, an alcali metal salt such as potassium or sodium acetate, and an organic nitrogen base, e.g. a tertiary amine such as triethylamine or triethanolamine. Suitable isomerizing agents include also hexamethylene-tetramine, benzyl-trimethylammonium hydroxide and sodium or potassium ter-butoxide. Sodium acetate and triethanolamine are however preferred.

The temperature at which the isomerization is effected is usually comprised in between 200° and 250° C, said values being however not limiting.

According to a preferred mode of operation, the isomerization is carried out in a reaction vessel equipped with a lateral fractionating column. Such an apparatus offers the advantage of enabling the isolation of progressively formed β-phorone from the reaction mixture.

A fraction comprising a ketonic mixture containing, together with the starting isophorone, β-phorone is thus obtained. Said fraction can be either directly subjected to the oxidation process of the invention, or further enriched in β-phorone by successive fractional distillations or by means of preparative vapour phase chromatography. It has to be appreciated however that the presence of starting isophorone in the mixture which has to oxidized does not have any adverse effect on the course of the oxidation itself. The invention is better illustrated by the following examples, wherein the temperatures are indicated in degrees centigrade and the abbreviations have the meaning common in the art.

EXAMPLE 1

A: 3,3,5-Trimethyl-cyclohex-4-en-1-one (β-phorone)

A mixture of 500 g of 3,3,5-trimethyl-cyclohex-5-en-1-one (isophorone) and 50 g of triethanolamine was refluxed for 4 hours, whereupon it was fractionally distilled to give a fraction at b.p. 170° C. The isomerization was performed in a reaction vessel equipped with a lateral distillation column having the following characteristics Height: 830 mm; filled up to 700 mm;
internal diameter: 24 mm;
filling: stainless steel springs of 5 mm length and 4 mm section.

The external temperature of the reaction vessel was kept at about 210°–250° during the whole operation.

435 g of β-phorone were thus obtained.

This mixture was then purified by vigorously mixing it with a 5 % agueous solution of tartaric acid and 125 ml of brine. Once upon separation, the organic phase was washed twice with 2 fractions of 250 ml each of brine and gave, after the usual treatments of drying and evaporation, 425 g of a mixture containing 71 % of β-phorone.

B: 2,2,6-Trimethyl-cyclohex-5-en-1,4-dione (oxophorone)

A mixture of 1380 g of a product obtained according to the hereinabove given process (β-phorone content: 51.6%) and 7 g of cobalt$^{III}$-acetylacetonate (Wacker Chemie GmbH, Munich, West Germany) was heated to about 50° under vigorous stirring (turbine speed: 1000 t/min). Air was then added to the said mixture at an initial flow of about 100–150 l/h, this flow being then progressively increased to about 300 l/h.

The reaction was exothermic, so that an external cooling proved to be necessary to maintain the temperature at about 56°–7°. Air was left bubbling through the reaction mixture for 30 hours, and the temperature was adjusted at about 50°; 8575 l of air were thus taken up. A sample of the reaction mixture indicated a peroxide index of 765. The mixture was distilled by means of a Vigreux column of 12 cm length to give 1040 g of a fraction having b.p. 40°–85°/0.1 Torr and a content of 38.1 % of the desired diketone. This latter was isolated in its pure form by further distillation by means of a fractionation column of 140 cm height and 24 mm section filled with stainless steel springs of 5×4 mm size. The product thus obtained showed the following analytical characteristics:

IR: 1710–1655 cm$^{-1}$ NMR (CCl$_4$): 1.2 (6H,s); 1.95 (3H,d,J 2 Hz); 2.65 (2H,s); 6.5 (1H,m) δ ppm; MS: M$^+$ = 152.

EXAMPLE 2

A mixture of 250 g of a product obtained in accordance with the procedure described in Example 1, paragraph A, whose β-phorone content was 89.5 %, and 1.25 g of iron$^{III}$-acetylacetonate was heated to about 50° under the vigorous stirring of a self-initiating turbine (speed: ca. 1000 t/min). The initial flow of air was of about 15 l/h, and it was progressively increased up to 120 l/h by increasing the turbine speed to 2000 t/min.

The reaction was exothermic and an external cooling was required in order to keep the temperature at about 58°–60°. The temperature was then lowered to 50°–2°.

A sample of reaction mixture indicated a peroxide index of 965, after 8 hours.

The whole mixture was then kept at 50° overnight thereafter a new control indicated a peroxide index of 220. The total taking up of air was of 2382 l. By operating as indicated in the previous example, 150 g of a mixture containing 78.6% of oxophorone were obtained.

The following table summarizes the reaction conditions used as well as the results achieved in a set of typical experiments carried out according to the above described procedure.

TABLE

| catalyst | reaction-time (h) | temperature (° C) | air flow (l/h) | catalyst concentration (%) | yield of 2,2,6-trimethyl-cyclohex-5-en-1,4-dione (%) |
|---|---|---|---|---|---|
| Oxidation in heterogeneous phase | | | | | |
| Mn$^{II}$ acetate | | | | | |
| Mg hydrogeno-carbonate | 39 | 50 | 150 | 1.5 Mn (OCOCH$_3$)$_2$ | 27.8 |
| Mn$^{III}$ acetate | 43 | 50 | 150 | 0.4 | 37.8 |
| Co$^{II}$ acetate /SiO$_2$ | 22.5 | 50 | 150 | 2 | 41.2 |
| Oxidation in homogeneous phase | | | | | |
| Co$^{II}$-acetylacetonate | 31 | 50 | 150 | 1 | 42.4 |
| Cr$^{III}$-acetylacetonate | 34 | 50 | 150 | 0.5 | 28.8 |
| V$^{III}$-acetylacetonate | 26 | 50 | 150 | 0.5 | 55.6 |
| Cu$^{II}$-acetylacetonate | 40 | 50 | 150 | 0.5 | 55 |
| Ni-acetylacetonate | 74 | 50 | 120 | 0.5 | |

In the course of the oxidation reaction, effected according to the above described example, the concomitant formation of certain amounts of 2,2,6-trimethyl-cyclohexane-1,4-dione, 3,3,5-trimethyl-cyclohex-5-en-4-ol-1-one and an enol-lactone of formula

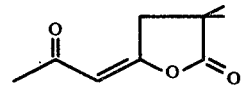

was observed.

What is claimed is:

1. Process for the preparation of 2,2,6-trimethyl-cyclohex-5-en-1-4-dione which comprises oxidizing, in the liquid phase, 3,3,5-trimethyl-cyclohex-4-en-1-one by means of oxygen or an oxygen containing gas mixture, in the presence of a metal catalyst essentially consisting of a member selected from the group consisting of acetate of manganese$^{II}$, manganese$^{III}$ of a cobalt$^{III}$, or an acetylacetonate of cobalt$^{II}$, of chromium$^{III}$, of vanadium$^{iii}$, of nickel$^{II}$or of copper$^{II}$.

2. A process according to claim 1 wherein the oxidation is effected at a temperature of from about 25° to 75° C.

3. A process according to claim 2 wherein the temperature is about 50° C.

* * * * *

UNITED STATES PATENT AND TRADEMARK OFFICE
CERTIFICATE OF CORRECTION

PATENT NO. : 4,026,948
DATED : May 31, 1977
INVENTOR(S) : Joseph J. Becker, Karl-Heinrich Schulte-Elte, Hugo Strickler and Gunther Ohloff It is certified that error appears in the above-identified patent and that said Letters Patent are hereby corrected as shown below:

Under References Cited, last line of Other Publications reads "Pergman Press Oxford (1975)"

should read --Pergman Press Oxford (1965)--

Column 5, line 19, reads "(3H,d,J 2 Hz)", should read

--(3H,d,J≈2 Hz)--

Signed and Sealed this

Twenty-seventh Day of September 1977

[SEAL]

Attest:

RUTH C. MASON
*Attesting Officer*

LUTRELLE F. PARKER
*Acting Commissioner of Patents and Trademarks*